United States Patent
Greenspan et al.

(10) Patent No.: US 11,969,362 B2
(45) Date of Patent: Apr. 30, 2024

(54) UPPER EXTREMITY PROSTHETIC WITH ENERGY RETURN SYSTEM

(71) Applicant: Accenture Global Solutions Limited, Dublin (IE)

(72) Inventors: Mark Benjamin Greenspan, Oakland, CA (US); Lavinia Andreea Danielescu, San Francisco, CA (US)

(73) Assignee: Accenture Global Solutions Limited, Dublin (IE)

( * ) Notice: Subject to any disclaimer, the term of this patent is extended or adjusted under 35 U.S.C. 154(b) by 31 days.

(21) Appl. No.: 17/242,632

(22) Filed: Apr. 28, 2021

(65) Prior Publication Data
US 2022/0117760 A1   Apr. 21, 2022

Related U.S. Application Data

(60) Provisional application No. 63/092,688, filed on Oct. 16, 2020.

(51) Int. Cl.
*A61F 2/68* (2006.01)
*A61F 2/50* (2006.01)
(Continued)

(52) U.S. Cl.
CPC .............. *A61F 2/68* (2013.01); *A61F 2/5044* (2013.01); *A61F 2/583* (2013.01); *A61F 2/70* (2013.01);
(Continued)

(58) Field of Classification Search
CPC .......... A61F 2/68; A61F 2/5044; A61F 2/583; A61F 2/70; A61F 2002/5075;
(Continued)

(56) References Cited

U.S. PATENT DOCUMENTS 3,263,983 A * 8/1966 Bliven ................. B60G 13/003
                                              267/225
3,603,142 A   9/1971 Saylak et al.
(Continued)

FOREIGN PATENT DOCUMENTS

EP        3254925         12/2017
WO    WO 2006/083913      8/2006
(Continued)

OTHER PUBLICATIONS

Adafruit.com [online], "USB LiIon/LiPoly charger—v1.2," available on or before Apr. 4, 2013 via Internet Archive: Wayback Machine URL<https://web.archive.org/web/20130404115906/https://www.adafruit.com/product/259>, retrieved on Sep. 3, 2021, retrieved from URL<https://www.adafruit.com/product/259>, 7 pages.
(Continued)

*Primary Examiner* — Ariana Zimbouski
*Assistant Examiner* — Maximilian Tobias Spencer
(74) *Attorney, Agent, or Firm* — Fish & Richardson P.C.

(57) ABSTRACT

An upper-extremity prosthetic is adapted to engage with an athletic ball. The prosthetic includes one or more springs that provide energy return as a user is throwing the ball using the prosthetic. The springs can have a conductivity that changes in relation to an amount of strain or deformation of the spring. The change in conductivity can be used to provide haptic feedback to the user so the user can sense the amount of force being applied to throw the ball. In some embodiments, the springs are made by a multi-material 3D printing (additive manufacturing) process and include a first material that is electrically non-conductive and a second material that is electrically conductive. In some embodiments, the prosthetic also includes one or more cantilevered springs that are also adapted to engage with the ball and to provide energy return while throwing the ball.

19 Claims, 9 Drawing Sheets

(51) Int. Cl.
  *A61F 2/58* (2006.01)
  *A61F 2/70* (2006.01)
  *F16F 1/36* (2006.01)
  *G01B 7/16* (2006.01)
(52) U.S. Cl.
  CPC .............. *F16F 1/3605* (2013.01); *G01B 7/18* (2013.01); *A61F 2002/5075* (2013.01); *A61F 2002/6827* (2013.01); *F16F 2226/04* (2013.01)
(58) Field of Classification Search
  CPC ............ A61F 2002/6827; F16F 1/3605; F16F 2226/04; G01B 7/16
  See application file for complete search history.

(56) References Cited

U.S. PATENT DOCUMENTS

| | | | | |
|---|---|---|---|---|
| 5,647,723 | A | * | 7/1997 | Rush .................... B25J 15/0009 901/29 |
| 6,500,210 | B1 | * | 12/2002 | Sabolich ................. A61F 2/583 623/24 |
| 9,352,629 | B2 | | 5/2016 | Chabanon et al. |
| 11,351,037 | B2 | * | 6/2022 | Jang ....................... A61F 2/4425 |
| 2005/0187640 | A1 | * | 8/2005 | Christensen .............. A61F 2/66 623/55 |
| 2005/0263962 | A1 | | 12/2005 | Roh et al. |
| 2006/0195197 | A1 | * | 8/2006 | Clausen .................... A61F 2/70 602/5 |
| 2008/0004140 | A1 | | 1/2008 | Matsumoto et al. |
| 2014/0041188 | A1 | * | 2/2014 | Radocy ................... A61F 2/588 29/428 |
| 2014/0046502 | A1 | * | 2/2014 | Schmitt ................. F16F 1/3615 701/1 |
| 2015/0033838 | A1 | * | 2/2015 | Chabanon .............. B60G 11/15 280/124.179 |
| 2018/0122768 | A1 | * | 5/2018 | Dugal ..................... H01L 25/11 |
| 2019/0254845 | A1 | * | 8/2019 | Wernke ..................... A61F 2/72 |
| 2020/0049648 | A1 | | 2/2020 | Kunc et al. |

FOREIGN PATENT DOCUMENTS

| | | |
|---|---|---|
| WO | WO 2018/204565 | 11/2018 |
| WO | WO 2020/102527 | 5/2020 |

OTHER PUBLICATIONS

Adidas.com [online], "4DFWD," available on or before Dec. 9, 2018 via Internet Archive: Wayback Machine URL<https://web.archive.org/web/20181209101026/https://www.adidas.com/us/4D>, retrieved on Sep. 3, 2021, retrieved from URL<https://www.adidas.com/us/4D>, 2 pages.
American Orthotic & Prosthetic Association, "O&P Almanac: Apr. 2016," Apr. 4, 2016, retrieved on Sep. 7, 2021, retrieved from URL<https://issuu.com/americanoandp/docs/april_2016_almanac>, 39 pages.
Autodesk.com [online], "Fusion 360," available on or before Jun. 29, 2013 via Internet Archive: Wayback Machine URL<https://web.archive.org/web/20130629013046/https://www.autodesk.com/products/fusion-360/overview>, retrieved on Sep. 3, 2021, retrieved from URL<https://www.autodesk.com/products/fusion-360/overview>, 6 pages.
Bandyopadhyay et al., "Additive manufacturing of multi-material structures," Mater. Sci. Eng. R Reports, Jul. 2018, 129:1-16.
Blank et al., "Identifying the Role of Proprioception in Upper-Limb Prosthesis Control: Studies on Targeted Motion," ACM Transactions on Applied Perception, Jun. 2010, 7(3):15, 23 pages.
Blickhan, "The Spring-mass Model for Running and Hopping," J. Biomechanics, 1989, 22(11-12):1217-1227.
BYU.edu [online], "Compliant Mechanisms Explained," available on or before Feb. 9, 2019 via Internet Archive: Wayback Machine URL<https://web.archive.org/web/20190209124255/https://www.compliantmechanisms.byu.edu/about-compliant-mechanisms>, retrieved on Sep. 3, 2021, retrieved from URL<https://www.compliantmechanisms.byu.edu/about-compliant-mechanisms>, 8 pages.
Carbon3D.com [online], "Rethinking foam—the Carbon lattice innovation," available on or before Sep. 26, 2020 via Internet Archive: Wayback Machine URL<https://web.archive.org/web/20200926042305/https://www.carbon3d.com/resources/whitepaper/rethinking-foam-carbons-lattice-innovation/>, retrieved on Sep. 3, 2021, retrieved from URL<https://www.carbon3d.com/resources/whitepaper/rethinking-foam-carbons-lattice-innovation/>, 11 pages.
Chuckit-toys.co.uk [online], "Chuckit! Sport Launcher," available on or before Apr. 28, 2016 via Internet Archive: Wayback Machine URL<https://web.archive.org/web/20160428080237/https://www.chuckit-toys.co.uk/our-products/launchers/chuckit-sport-launcher.html>, retrieved on Sep. 3, 2021, retrieved from URL<https://www.chuckit-toys.co.uk/our-products/launchers/chuckit-sport-launcher.html>, 2 pages.
EnablingTheFuture.com [online], "Enabling The Future," available on or before Feb. 28, 2014 via Internet Archive: Wayback Machine URL<https://web.archive.org/web/20140228201637/http://enablingthefuture.org/>, retrieved on Sep. 3, 2021, retrieved from URL<http://enablingthefuture.org/>, 7 pages.
Engadget.com [online], "Haptic feedback gives prosthetics 'muscle sense'," May 30, 2017, retrieved on Sep. 3, 2021, retrieved from URL<https://www.engadget.com/2017-05-30-haptic-feedback-gives-prosthetics-muscle-sense.html?guccounter=1&guce_referrer=aHR0cHM6Ly93d3cuZ29vZ2xILmNvbS8&guce_referrer_sig=AQAAAGrzAbBDwDyl3TDp3RcPkh6rLUpaliA6sCUFBoPnD_IaWLNna-0dnMOiCM-tkL_C8DqiglsP3lasYnCykzQMYZQ42nChyMNBqNHSWIQjpiGXQSotwyxxIZzWMMuM8B5rf8zM7Z2k9Qzkdm5WWyPIL6uvPLB3zrJkTo2nwedKSFBe>, 4 pages.
Farserotu et al., "Tactile Prosthetics in WiseSkin," Presented at Proceedings of the 2015 Design, Automation & Test in Europe Conference & Exhibition, Grenoble, France, Mar. 9-13, 2015, 1695-1697.
Formlabs.com [online], "Guide to Stereolithography (SLA) 3D Printing," available on or before Apr. 26, 2017 via Internet Archive: Wayback Machine URL<https://web.archive.org/web/20170426223030/https://formlabs.com/blog/ultimate-guide-to-stereolithography-sla-3d-printing/>, retrieved on Sep. 3, 2021, retrieved from URL<https://formlabs.com/blog/ultimate-guide-to-stereolithography-sla-3d-printing/>, 30 pages.
Greenspan et al., "Designing Low-Cost Sports Prosthetics with Advanced 3D Printing Techniques," Presented at Proceedings of UIST '20 Adjunct: Adjunct Publication of the 33rd Annual ACM Symposium on User Interface Software and Technology, Oct. 20, 2020, 126-128.
He et al., "Ondulé: Designing and Controlling 3D Printable Springs," Presented at Proceedings of the 32nd Annual ACM Symposium on User Interface Software and Technology, New Orleans, LA, USA, Oct. 20-23, 2019, 739-750.
Humphreys et al., "The Size and Scope of the Sports Industry in the United States: Estimates of the Size of the Sports Industry in the United States," Presented at Proceedings of the 10th Annual IASE Conference, Gijón, Spain, May 2008, 40 pages.
Hung et al., "Finger and Palm Dynamic Pressure Monitoring for Basketball Shooting," J. Sensors, May 2017, 2017(2):1-5.
Matthews et al., "Return to sport following an amputation," J. Sports Med. Phys. Fitness, Aug. 2014, 54(4):481-486.
Nemah et al., "A Review of Non-Invasive Haptic Feedback stimulation Techniques for Upper Extremity Prostheses," Int. J. Integr. Engineering, Apr. 2019, 11(1):299-326.
Okubo et al., "Kinematics of Arm Joint Motions in Basketball Shooting," Procedia Engineering, 2015, 112:443-448.
Ossur.com [online], "Flex-Foot Cheetah," available on or before Nov. 11, 2020 via Internet Archive: Wayback Machine URL<https://web.archive.org/web/20201111162754/https://www.ossur.com/en-us/prosthetics/feet/flex-foot-cheetah>, retrieved on Sep. 7, 2021, retrieved from URL<https://www.ossur.com/en-us/prosthetics/feet/flex-foot-cheetah>, 7 pages.
OT4-Orthopaedietechnik.com [online], "Products," available on or before Mar. 24, 2019 via Internet Archive: Wayback Machine

(56) References Cited

OTHER PUBLICATIONS

URL<https://web.archive.org/web/20190324064459/https://www.ot4-orthopaedietechnik.com/Produkte>, retrieved on Sep. 7, 2021, retrieved from URL<https://www.ot4-orthopaedietechnik.com/produkte>, 2 pages (with English translation).
Pinshape.com [online], ""Spock" Basketball Prosthetic Hand," available on or before Mar. 7, 2021 via Internet Archive: Wayback Machine URL<https://web.archive.org/web/20210307051825/https://pinshape.com/items/24569-3d-printed-spock-basketball-prosthetic-hand>, retrieved on Sep. 3, 2021, retrieved from URL<https://pinshape.com/items/24569-3d-printed-spock-basketball-prosthetic-hand>, 9 pages.
Proto-pasta.com [online], "Electrically Conductive Composite PLA," available on or before May 7, 2015 via Internet Archive: Wayback Machine URL<https://web.archive.org/web/20150507001513/https://www.proto-pasta.com/products/conductive-pla>, retrieved on Sep. 7, 2021, retrieved from URL<https://www.proto-pasta.com/products/conductive-pla>, 5 pages.
Psyonic.io [online], "The Ability Hand," upon information and belief, available no later than Oct. 16, 2020, retrieved on Sep. 7, 2021, retrieved from URL<https://www.psyonic.io/ability-hand>, & pages.
Schmidt et al., "3D-printed prosthetics for the developing world," Presented at Proceedings of SIGGRAPH '15: Special Interest Group on Computer Graphics and Interactive Techniques Conference, Los Angeles, CA, USA, Aug. 9-13, 2015, Article No. 21, 1 page.
Skylar-Scott et al., "Voxelated soft matter via multimaterial multinozzle 3D printing, " Nature, Nov. 13, 2019, 575(7783):330-335.
Struzik et al., "Biomechanical Analysis of the Jump Shot in Basketball," J. Hum. Kinetics, Sep. 29, 2014, 42:73-79.
Tong et al., "Low-cost sensor-integrated 3D-printed personalized prosthetic hands for children with amniotic band syndrome: A case study in sensing pressure distribution on an anatomical human-machine interface (AHMI) using 3D-printed conformal electrode arrays," PLoS One, Mar. 28, 2019, 14(3):e0214120, 23 pages.
TRSProsthetics.com [online], "Hoopster," available on or before Apr. 19, 2016 via Internet Archive: Wayback Machine URL<https://web.archive.org/web/20160419155343/https://www.trsprosthetics.com/product/basketball-hoopster/>, retrieved on Sep. 7, 2021, retrieved from URL<https://www.trsprosthetics.com/product/basketball-hoopster/>, 2 pages.
Ultimaker, "Technical data sheet PLA," Version 4.002, dated Nov. 19, 2018, 3 pages.
Ultimaker, "Technical data sheet TPU 95A," Version 3.010, dated May 16, 2017, 3 pages.
Ultimaker.com [online], "Ultimaker Cura," available on or before Jul. 3, 2019 via Internet Archive: Wayback Machine URL<https://web.archive.org/web/20190703062848/https://ultimaker.com/software/ultimaker-cura>, retrieved on Sep. 7, 2021, retrieved from URL<https://ultimaker.com/software/ultimaker-cura>, 11 pages.
Ultimaker.com [online], "Ultimaker S5," available on or before Dec. 12, 2019 via Internet Archive: Wayback Machine URL<https://web.archive.org/web/20191212042119/https://ultimaker.com/3d-printers/ultimaker-s5>, retrieved on Sep. 7, 2021, retrieved from URL<https://ultimaker.com/3d-printers/ultimaker-s5>, 9 pages.
USAB.com [online], "The Basic Jump Shot," dated Oct. 30, 2014, retrieved on Sep. 7, 2021, retrieved from URL<https://www.usab.com/youth/news/2010/01/the-basic-jump-shot.aspx>, 12 pages.
Ziegler-Graham et al., "Estimating the Prevalence of Limb Loss in the United States: 2005 to 2050," Arch. Phys. Med. Rehabilitation, Mar. 2008, 89(3):422-429.
EP Partial Search Report in European Appln. No. 21194614.0, dated Mar. 1, 2022, 10 pages.
EP Extended Search Report in European Appln. No. 21194614.0, dated Jun. 30, 2022, 10 pages.
[No Author], "Amputation Data from Community Hospitals," O&P Almanac, Apr. 2016, 1 page.
Adidas.com [online], "4D Shoes & Sneakers," available on or before May 13, 2019 via Internet Archive: Wayback Machine URL<https://web.archive.org/web/20190513141233/https://www.adidas.com/us/4d-shoes>, retrieved on Sep. 15, 2022, retrieved from URL<https://www.adidas.com/us/4d-shoes>, 10 pages.
Bowen et al., "A Low-Cost Customizable Prosthetic Foot with Energy Return Capabilities," Prosthetics and Orthotics Open Journal, Jan. 8, 2018, 2(1:1):1-5.
Brancazio, "Physics of basketball," Am. J. Physics, Jul. 28, 1998, 49(4):356-365.
Chen et al., "Advances in Responsively Conductive Polymer Composites and Sensing Applications," Polym. Reviews, Mar. 10, 2020, 61(1):157-193.
Chiang et al., "Coordination of Basketball Shooting Movement of Different Skill Level Players," Presented at Proceedings of the 24th International Symposium on Biomechanics in Sports, Salzburg, Austria, Jul. 14-18, 2006, 4 pages.
Childers et al., "Increasing prosthetic foot energy return affects whole-body mechanics during walking on level ground and slopes," Sci. Reports, Mar. 29, 2018, 8(1):5354, 12 pages.
Comotti et al., "Multi-Material Design and 3D Printing Method of Lower Limb Prosthetic Sockets," Presented at Proceedings of the 3rd 2015 Workshop on ICTs for Improving Patients Rehabilitation Research Techniques (REHAB '15), Lisbon, Portugal, Oct. 1-2, 2015, 42-45.
Faber et al., "Bioinspired spring origami," Science, Mar. 23, 2018, 359(6382):1386-1391.
Fuss, "Closing the gap through technology," Sports Technology, Nov. 8, 2010, 1(4-5):169-171.
Gao et al., "RevoMaker: Enabling Multi-Directional and Functionally-Embedded 3D Printing Using a Rotational Cuboidal Platform," Presented at Proceedings of the 28th Annual ACM Symposium on User Interface Software & Technology (UIST '15), Charlotte, NC, USA, Nov. 11-15, 2015, 437-446.
Garanger et al., "3D Printing of a Leaf Spring: A Demonstration of Closed-Loop Control in Additive Manufacturing," Presented at Proceedings of the 2018 IEEE Conference on Control Technology and Applications (CCTA), Copenhagen, Denmark, Aug. 21-24, 2018, 465-470.
Gong et al., "MetaSense: Integrating Sensing Capabilities into Mechanical Metamaterial," Presented at Proceedings of the 34th Annual ACM Symposium on User Interface Software and Technology (UIST '21), Virtual Event, USA, Oct. 10-14, 2021, 1063-1073.
Goudswaard et al., "FabriClick: Interweaving Pushbuttons into Fabrics Using 3D Printing and Digital Embroidery," Presented at Proceedings of the 2020 ACM Designing Interactive Systems Conference (DIS '20), Eindhoven, Netherlands, Jul. 6-10, 2020, 379-393.
Grønborg et al., "Conductive Compliant Mechanisms: Geometric tuning of 3D printed flexural sensors," Addit. Manuf. Letters, Sep. 6, 2022, 100088, 15 pages.
Houdijk et al., "Energy storing and return prosthetic feet improve step length symmetry while preserving margins of stability in persons with transtibial amputation," J. Neuroeng. Rehabilitation, Sep. 5, 2018, 15(Suppl 1):76, 8 pages.
Humphreys et al., "The Size and Scope of the Sports Industry in the United States," IASE/NAASE Working Paper Series, Aug. 2008, No. 08-11, 39 pages.
Instructables.com [online], ""Spock" Prosthetic Basketball Hand," upon information and belief, available no later than Oct. 16, 2020, retrieved on Sep. 15, 2022, retrieved from URL<https://www.instructables.com/Spock-Prosthetic-Basketball-Hand-by-UCLA-3D4E/>, 19 pages.
Leigh et al., "A Simple, Low-Cost Conductive Composite Material for 3D Printing of Electronic Sensors," PLoS One, Nov. 21, 2012, 7(11):e49365, 6 pages.
Malone et al., "Shooting mechanics related to player classification and free throw success in wheelchair basketball," J. Rehabil. Res. Development, Nov./Dec. 2002, 39(6):701-709.
Nolan, "Carbon fibre prostheses and running in amputees: A review," Foot Ankle Surgery, Jul. 14, 2008, 14(3):125-129.
Okubo et al., "Rebounds of basketball field shots," Sports Engineering, Oct. 14, 2014, 18(1):43-54.
Olesnavage et al., "Analysis of Rollover Shape and Energy Storage and Return in Cantilever Beam-Type Prosthetic Feet," Presented at

(56) References Cited

OTHER PUBLICATIONS

Proceedings of the ASME 2014 International Design Engineering Technical Conferences and Computers and Information in Engineering Conference (IDETC/CIE 2014), Buffalo, NY, USA, Aug. 17-20, 2014, 10 pages.
OpenBionics.com [online], "Meet the Hero Arm—a prosthetic arm for adults and children," available on or before Mar. 30, 2018 via Internet Archive: Wayback Machine URL<https://web.archive.org/web/20180330052341/https://openbionics.com/hero-arm/>, retrieved on Sep. 15, 2022, retrieved from URL<https://openbionics.com/hero-arm/>, 20 pages.
Podmenik et al., "The effect of shooting range on the dynamics of limbs angular velocities of the basketball shot," Kinesiology, 2017, 49(1):92-100.
Ray et al., "Prosthetic energy return during walking increases after 3 weeks of adaptation to a new device," J. Neuroeng. Rehabilitation, Jan. 27, 2018, 15(1):6, 8 pages.
Rocha et al., "Fabrication and characterization of bending and pressure sensors for a soft prosthetic hand," J. Micromech. Microengineering, Jan. 17, 2018, 28(3):034001, 24 pages.
Rojas et al., "Kinematic adjustments in the basketball jump shot against an opponent," Ergonomics, Oct. 2000, 43(10):135-144.
Saggio et al., "Flex sensor characterization against shape and curvature changes," Sens. Actuator A Physical, Apr. 15, 2018, 273:221-231.
Shigleys Mechanical Engineering Design, 11th ed., Budynas et al. (eds.), 2019, 1116 pages.
TRSProsthetics.com [online], "Body Powered Prosthetic Simulator," available on or before Dec. 22, 2015 via Internet Archive: Wayback Machine URL<https://web.archive.org/web/20151222233207/https://www.trsprosthetics.com/product/body-powered-prosthetic-simulator/>, retrieved on Sep. 15, 2022, retrieved from URL<https://www.trsprosthetics.com/product/body-powered-prosthetic-simulator/>, 4 pages.
TRSProsthetics.com [online], "Sports—Prosthetics for Sports & Activities," available on or before Dec. 13, 2015 via Internet Archive: Wayback Machine URL<https://web.archive.org/web/20151213154816/http://www.trsprosthetics.com/shop-category/sports/>, retrieved on Sep. 15, 2022, retrieved from URL<https://www.trsprosthetics.com/shop-category/sports/>, 9 pages.
Ultimaker.com [online], "Ultimaker PLA," available on or before May 15, 2020 via Internet Archive: Wayback Machine URL<https://web.archive.org/web/20200515043326/https://ultimaker.com/materials/pla>, retrieved on Feb. 10, 2022, retrieved from URL<https://ultimaker.com/materials/pla>, 5 pages.
Ultimaker.com [online], "Ultimaker TPU 95A," available on or before Jun. 17, 2020, via Internet Archive: Wayback Machine URL<https://web.archive.org/web/20200617042640/https://ultimaker.com/materials/tpu-95a>, retrieved on Sep. 15, 2022, retrieved from URL<https://ultimaker.com/materials/tpu-95a>, 4 pages.
Walker et al., "Recreational Terminal Devices for Children With Upper Extremity Amputations," J. Pediatr. Orthopedics, Mar. 2008, 28(2):271-273.
Wolterink et al., "A 3D-Printed Soft Fingertip Sensor for Providing Information about Normal and Shear Components of Interaction Forces," Sensors, Jun. 22, 2021, 21(13):4271, 13 pages.
Wright et al., "Prosthetic usage in major upper extremity amputations," J. Hand Surgery, Jul. 1, 1995, 20(4):619-622.
Yoshii et al., "Measurement of wrist flexion and extension torques in different forearm positions," Biomed. Eng. Online, Dec. 12, 2015, 14:115, 10 pages.
Zelik et al., "Systematic Variation of Prosthetic Foot Spring Affects Center-of-Mass Mechanics and Metabolic Cost During Walking," IEEE Trans. Neural Syst. Rehabil. Engineering, Aug. 2011, 19(4):411-419.
Zolfagharian et al., "3D printing non-assembly compliant joints for soft robotics," Results in Engineering, Sep. 2022, 15:100558, 10 pages.
EP Extended Search Report in European Appln. No. 23154052.7, dated May 16, 2023, 7 pages.

\* cited by examiner

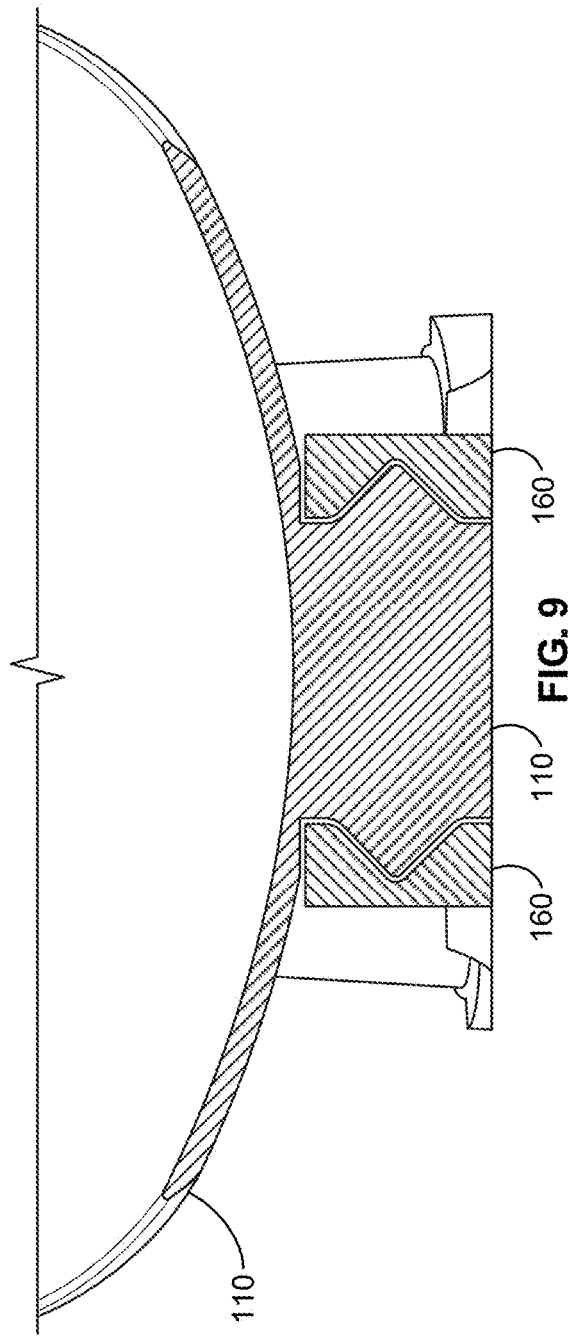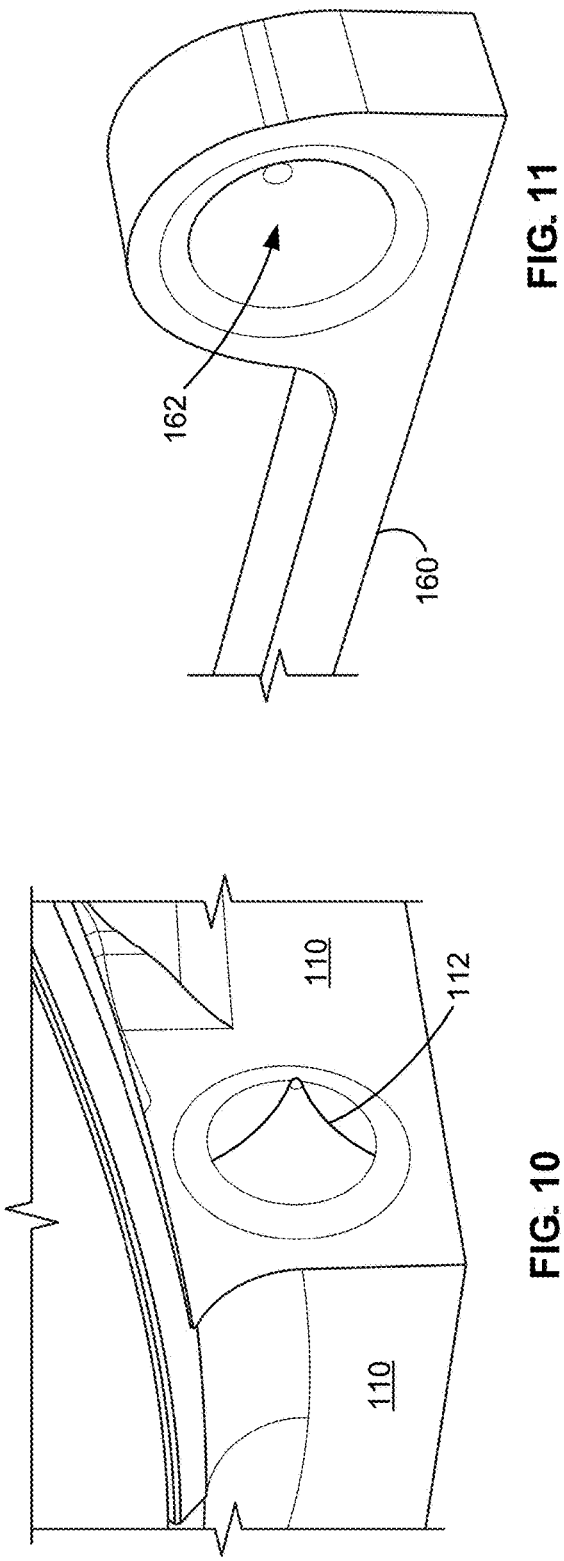

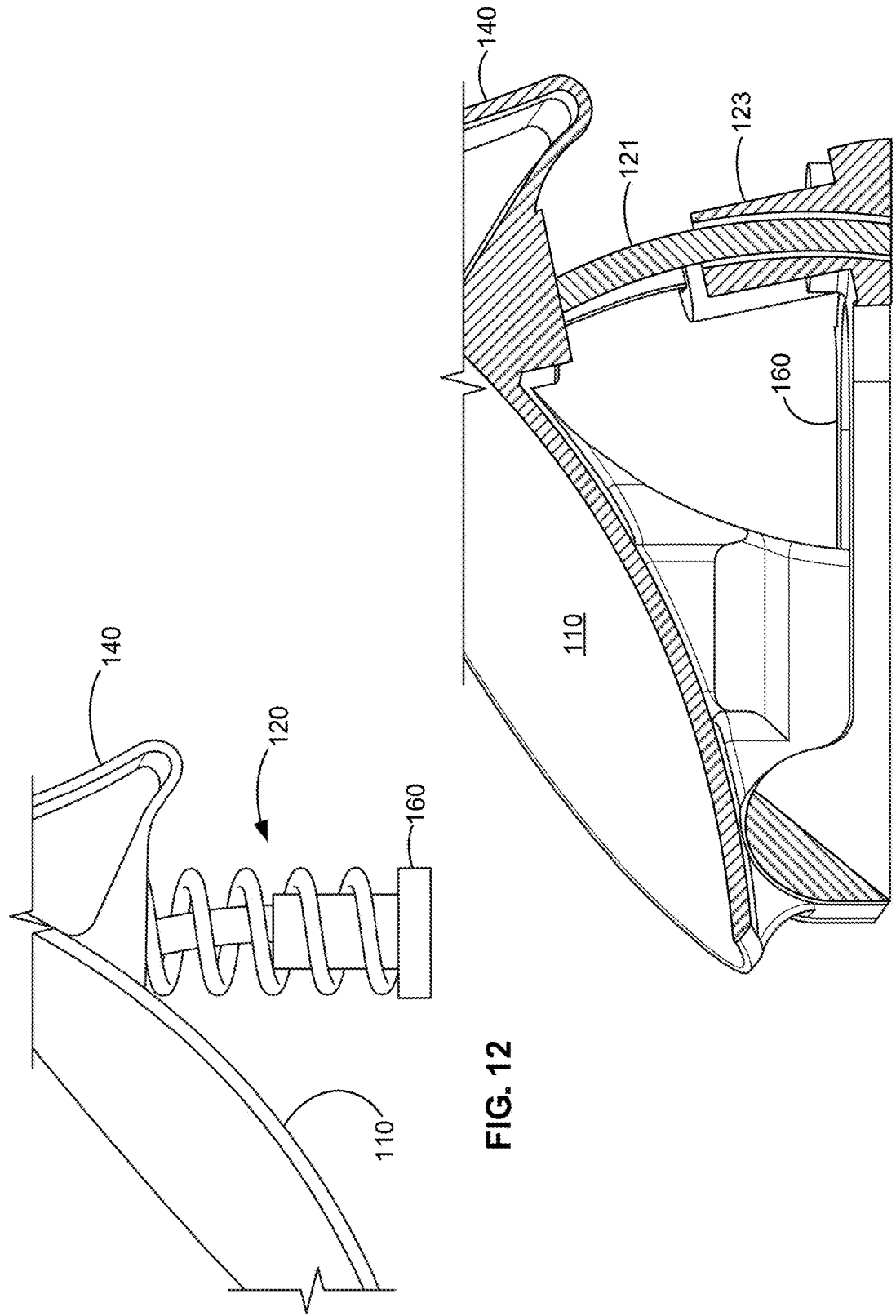

UPPER EXTREMITY PROSTHETIC WITH ENERGY RETURN SYSTEM

CROSS-REFERENCE TO RELATED APPLICATION

This application claims the benefit of U.S. Provisional Application Ser. No. 63/092,688 filed Oct. 16, 2020. The disclosure of the prior application is considered part of (and is incorporated by reference in) the disclosure of this application.

TECHNICAL FIELD

This disclosure generally relates to prosthetics.

BACKGROUND 3D printing is a widely used manufacturing technique for both commercial products and research across many industries with emerging research areas in multi-material 3D printing, metamaterials, and 3D printed electronics. Because of the high customizability and accessibility 3D printing offers, more mechanisms such as prosthetics are being 3D printed. However, conventional 3D printed prosthetics do not allow for the same function and control that a natural limb provides. For example, a natural limb allows a person to feel how hard they are grasping an object.

As of 2020, there are roughly two million people living in the USA with limb loss. Of those, there are over ten times as many lower limb amputations as there are upper limb amputations leading to a large number of lower extremity prosthetic solutions. The upper extremity, and specifically the hand, is responsible for the vast majority of high dexterity and fine control tasks performed by an individual. The high dexterity required makes designing a functional prosthetic hand significantly more complex. Upper extremity prosthetics offer a range of fine motor control, but the majority are only designed for grasping tasks. Existing prosthetics are limited in their functionality because they don't give positional or force feedback which are critical features for sports specific prosthetics.

Athletes who play sports have few options for sport specific prosthetics and those that exist do not provide the high degree of dexterity and control that allows an individual to excel. Research shows that athletes or individuals who return to playing sports after an amputation have improved psychological health. Basketball is the most common ball sport played and the seventh most common recreational sport. In addition, the force applied from wrist and finger flexion on a basketball is extremely important to control the speed, direction and spin of the ball. For these reasons, a basketball prosthetic hand is helpful.

SUMMARY

In general, an aspect of the subject matter described in this specification may involve a prosthetic. The prosthetic includes a coil spring that provides energy return and that has a conductivity that varies in relation to an amount of strain on the spring. In some embodiments, the springs are made by multi-material 3D printing (additive manufacturing). Such springs made by multi-material 3D printing may include a first material that is electrically non-conductive (insulative) and a second material that electrically conductive. The extent of the deformation or strain of the spring may be determined or estimated by measuring the conductivity or resistivity of the electrically conductive material portion of the spring. A haptic feedback generator may generate haptic feedback to the user proportionate to the conductivity (and the deformation) of the coil spring. Accordingly, the energy returned by the coil spring may help a wearer of the prosthetic perform a task with less energy, and the haptic feedback may help the wearer perform the task with more fine-tuned control.

Some inventive aspects described herein include, but are not limited to: (i) an upper-extremity prosthetic that is adapted to engage with an athletic ball, (ii) springs that provide energy return as a user is throwing the ball using the prosthetic, (iii) the springs can have a conductivity that changes in relation to an amount of strain or deformation of the spring, and (iv) the change in conductivity can be used to provide haptic feedback to the user so the user can sense the amount of force being applied while throwing the ball.

In some embodiments, the prosthetic devices described herein can be made by a 3D printing (additive manufacturing) process. In particular embodiments, one or more of the springs of the prosthetic devices are made by a multi-material 3D printing process and include a first material that is electrically non-conductive and a second material that electrically conductive. In some embodiments, the prosthetic also includes one or more cantilevered springs that are also adapted to engage with the ball and to provide energy return while a user of the prosthetic is throwing the ball.

The use of one or more springs with integrated strain sensing capabilities for the prosthetic described herein may reduce the number of electronic components, reduce the steps for assembly after fabrication, and reduce the weight and overall cost in comparison to other techniques such as the use of a traditional accelerometer or pressure sensor.

In some aspects, this disclosure is directed to an upper-extremity prosthetic. Such an upper-extremity prosthetic includes a first member having a surface adapted to engage with an athletic ball and a first spring coupled to the first member. The first spring is arranged to absorb energy and to provide energy return in response to movement of the first member. The first spring has a conductivity that changes in response to deflection of the first spring. The upper-extremity prosthetic also includes electrical circuitry configured to detect the conductivity of the first spring and to output a signal responsive to the conductivity.

Such an upper-extremity prosthetic may optionally include one or more of the following features. The upper-extremity prosthetic may also include a base member coupled to the first spring and pivotably coupled to the first member. In some embodiments, pivoting the first member relative to the base member deflects the first spring. The upper-extremity prosthetic may also include a sleeve coupled to the base member and defining an interior space configured to receive a residual limb of a user of the prosthetic. The upper-extremity prosthetic may also include a haptic device arranged to receive the signal responsive to the conductivity from the electrical circuitry. The haptic device may be a vibratory motor arranged to vibrate against a residual limb in the interior space. The upper-extremity prosthetic may also include a first cantilever spring coupled to the first member and including a surface arranged to engage with an athletic ball engaged with the first member. The upper-extremity prosthetic may also include a first cantilever spring coupled to the first member and a second cantilever spring coupled to the first member. The second and third springs may each include a surface arranged to engage with an athletic ball engaged with the first member. The surfaces of the first member, the first cantilever spring, and the second cantilever spring may each be contoured to engage with an athletic ball. The first spring may be a multi-material 3D printed device. In some embodiments, the first spring and the first member are 3D printed in a single print process.

In another aspect, this disclosure is directed to an upper-extremity prosthetic that includes a first member having a surface adapted to engage with an athletic ball, a first spring coupled to the first member and arranged to deflect and to provide energy return in response to movement of the first member, and a first cantilever spring extending from the first member and having a surface adapted to engage with an athletic ball while the athletic ball is also engaged with the surface of the first member.

Such an upper-extremity prosthetic may optionally include one or more of the following features. The upper-extremity prosthetic may also include a second cantilever spring extending from the first member and having a surface adapted to engage with an athletic ball while the athletic ball is also engaged with the surface of the first member. The upper-extremity prosthetic may also include a second spring coupled to the first member and arranged to deflect and to provide energy return in response to movement of the first member. The first and second springs may each be coil springs. The upper-extremity prosthetic may also include a base member coupled to the first spring and pivotably coupled to the first member. Pivoting the first member relative to the base member may deflect the first spring. The upper-extremity prosthetic may also include a sleeve coupled to the base member and defining an interior space configured to receive a residual limb of a user of the prosthetic. The base member, the first member, the first spring, and the first cantilever spring member may each be 3D printed in a single print process. In some embodiments, the first spring is a multi-material 3D printed device and includes: a first 3D printed material; a second 3D printed material integrated with the first 3D printed material and having an electrical conductivity that is greater than an electrical conductivity of the first 3D printed material; a first electrical contact connected to the second 3D printed material; and a second electrical contact connected to the second 3D printed material. The first spring may be configured to have an electrical conductivity between the first and second electrical contacts that changes in response to deformation of the spring. The upper-extremity prosthetic may also include electrical circuitry configured to detect the electrical conductivity of the first spring between the first and second electrical contacts, and to output a signal responsive to the electrical conductivity. The upper-extremity prosthetic may also include a haptic device arranged to receive the signal responsive to the electrical conductivity from the electrical circuitry, and wherein the haptic device is a vibratory motor arranged to vibrate against a limb of a user of the prosthetic.

The details of one or more implementations are set forth in the accompanying drawings and the description, below. Other potential features and advantages of the disclosure will be apparent from the description and drawings, and from the claims.

BRIEF DESCRIPTION OF THE DRAWINGS

FIGS. 9-11 illustrate an example pivot mechanism of the prosthetic hand of FIG. 1.

FIGS. 12-15 illustrate an example spring mechanism of the prosthetic hand of FIG. 1.

Like reference symbols in the various drawings indicate like elements.

DETAILED DESCRIPTION

Figure 1:
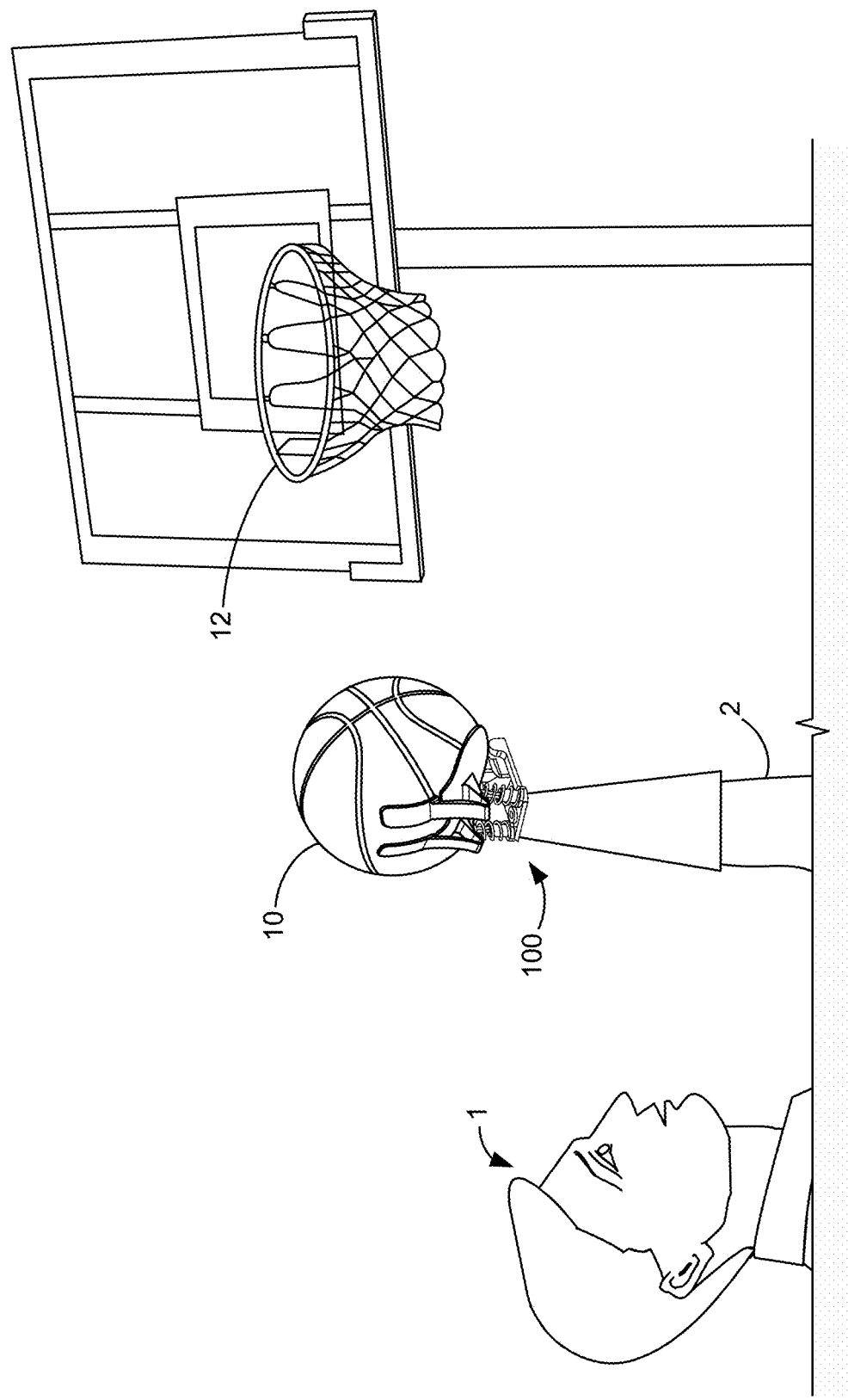
FIG. 1 illustrates a person preparing to shoot a basketball using an example prosthetic hand in accordance with some embodiments.
Figure 2:
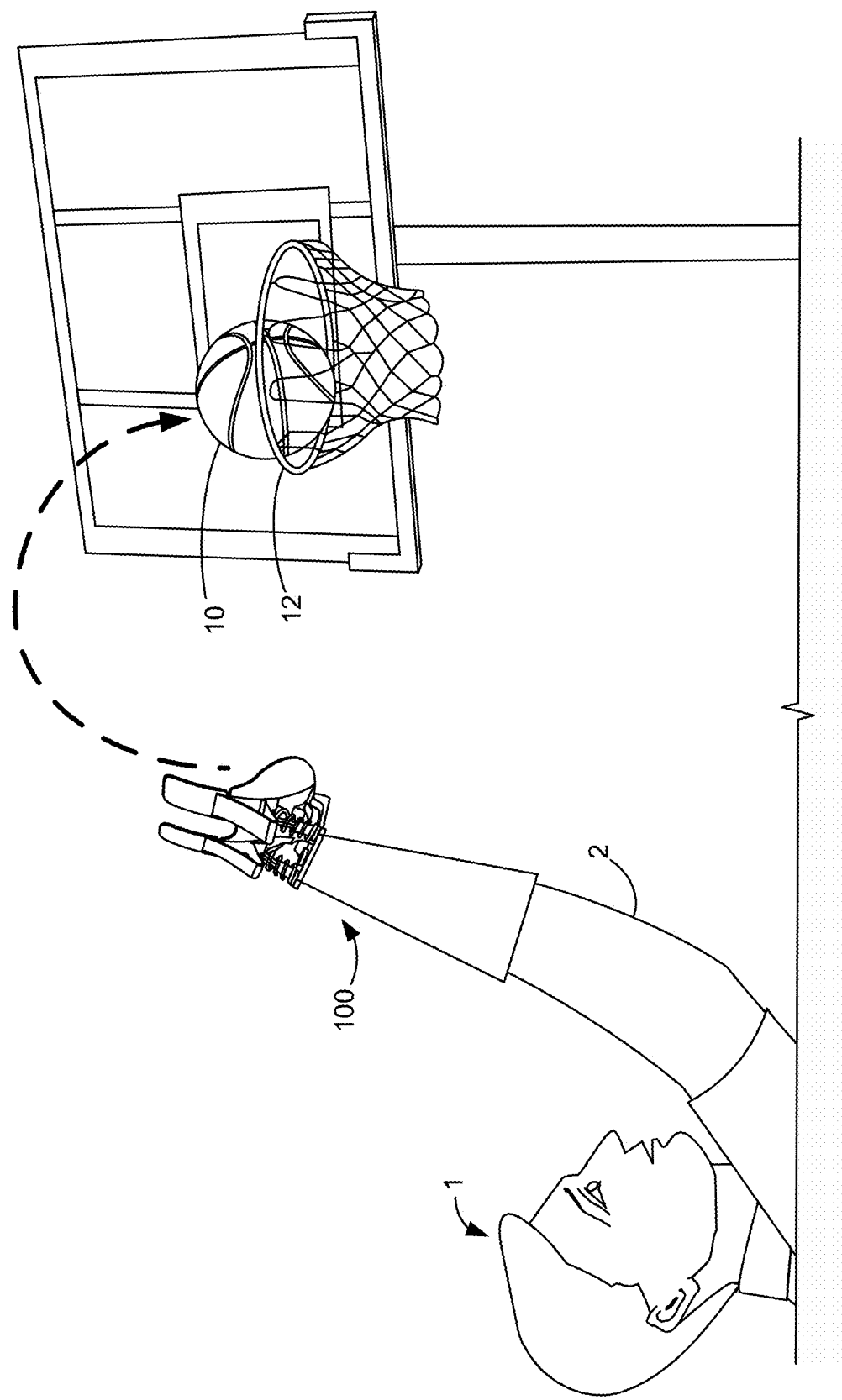
FIG. 2 illustrates the person and prosthetic hand of FIG. 1 after shooting the basketball.

Referring to FIGS. 1 and 2, an example upper-extremity prosthetic 100 can be worn by a user 1 (e.g., an amputee) to, for example, shoot a basketball 10 into a basketball goal 12. As described further below, in some embodiments the prosthetic 100 includes one or more springs, and can include a haptic feedback system that provides the user 1 with a physical sensation that is proportional to the amount of force applied to the basketball 10 via the prosthetic 100 during the shot. Accordingly, the energy returned by the spring(s) may help the user 1 shoot the basketball 10 while using less energy, and the haptic feedback may help the user 1 shoot the basketball 10 with more fine-tuned control.

While the scenario depicted here is a basketball shot, the design aspects of the prosthetic 100 described below can also be applied for prosthetics adapted for use in other contexts. For example, the concepts described herein can be applied in prosthetics adapted for purposes such as, but not limited to, throwing a football, throwing an item such as a baseball or softball, throwing a flying disc, dribbling a ball, and the like, without limitation.

Figure 3:
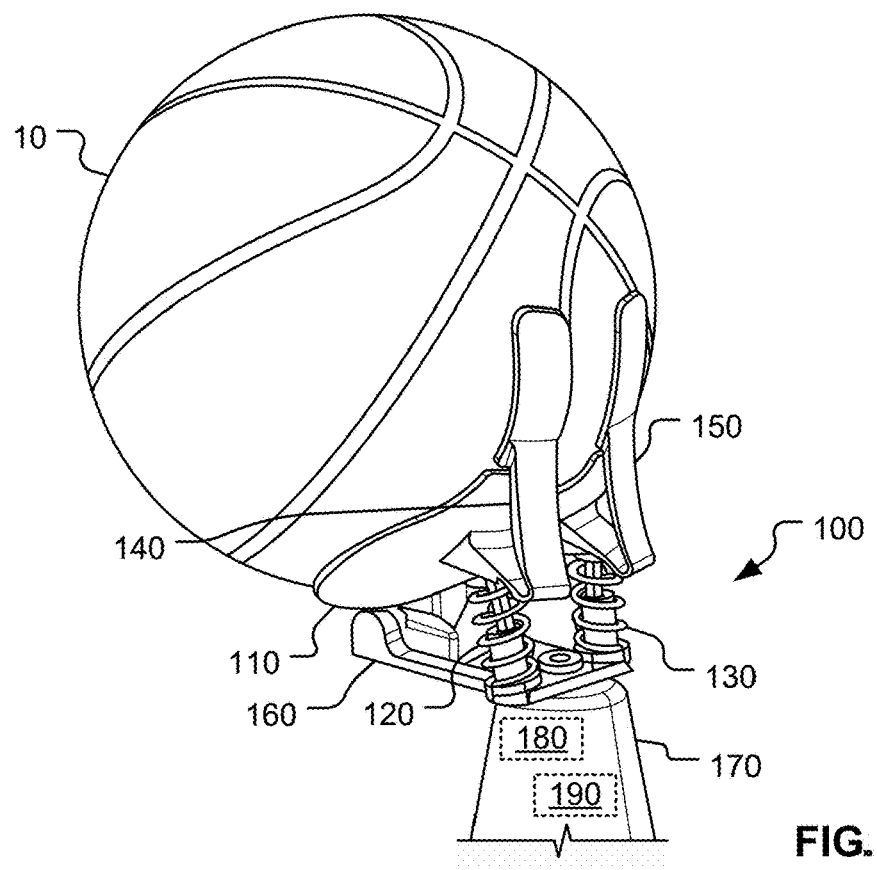
FIG. 3 is a perspective view of the prosthetic hand of FIG. 1 in engagement with the basketball.
Figure 4:
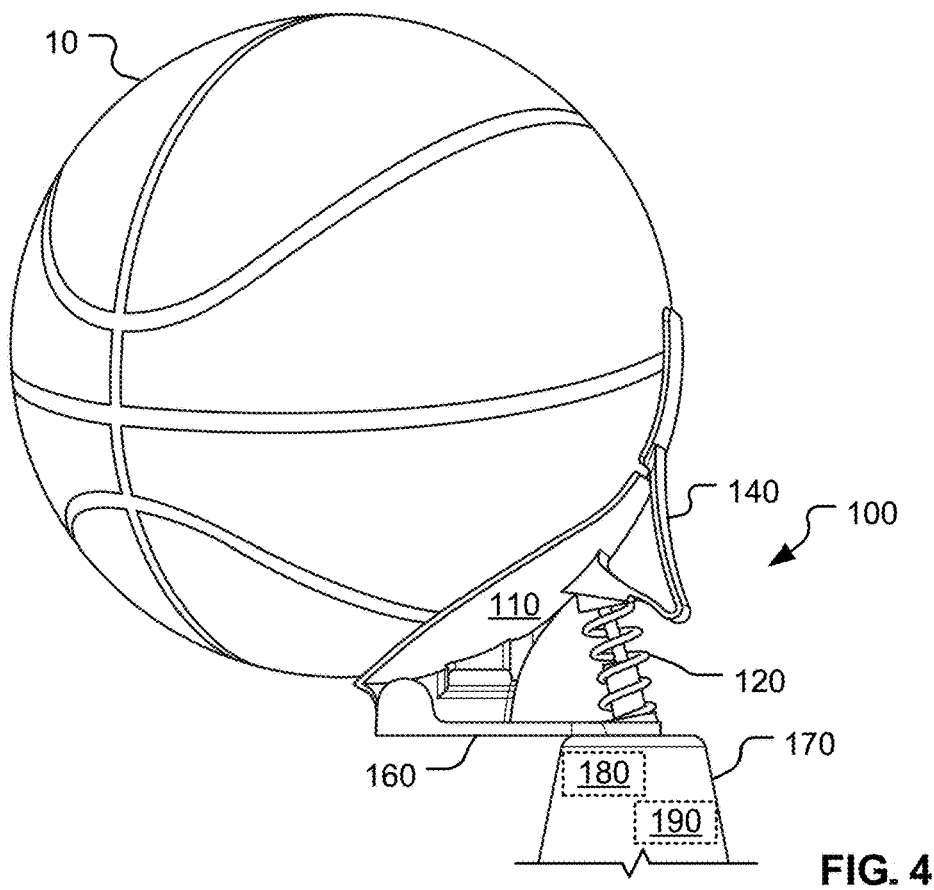
FIG. 4 is a side view of the prosthetic hand of FIG. 1 in engagement with the basketball.
Figure 5:
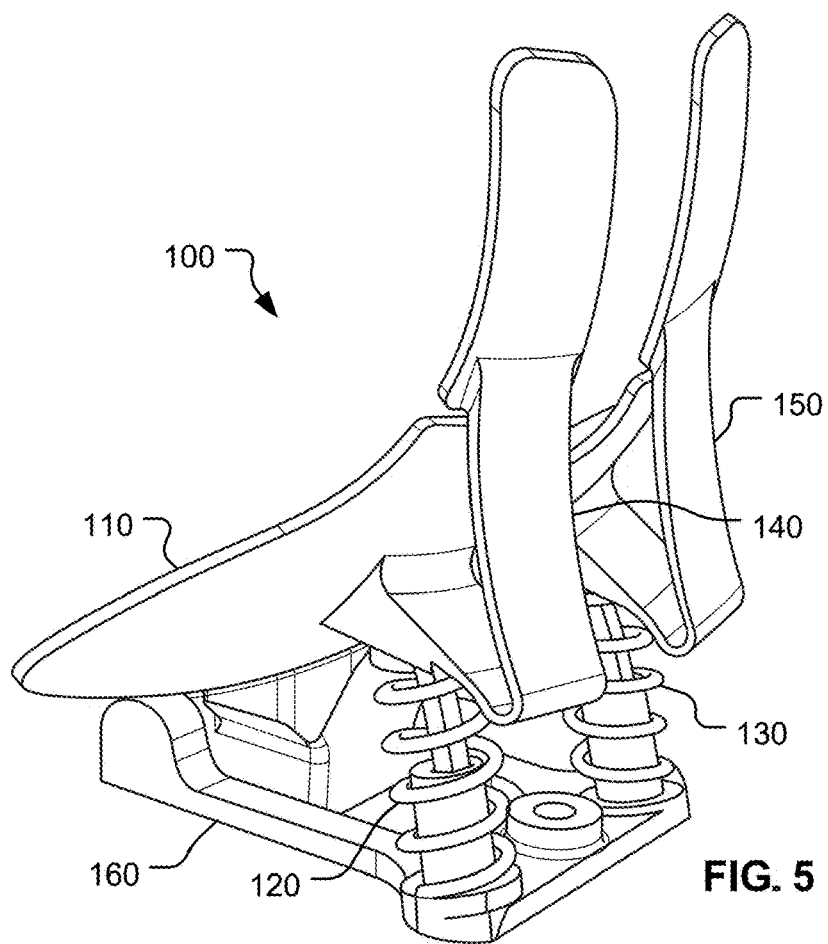
FIG. 5 is another perspective view of the prosthetic hand of FIG. 1.

Referring to FIGS. 3-5, the prosthetic 100 includes a first member 110, a first spring 120, a second spring 130, a first cantilever spring 140, a second cantilever spring 150, a base member 160, a socket 170, electrical circuitry 180, and a haptic device 190. At least the following components of the prosthetic 100 are optional and not included in some embodiments of the prosthetic 100: the second spring 130, the second cantilever spring 150, the socket 170, the electrical circuitry 180, and the haptic device 190. For example, in some embodiments the prosthetic 100 can include just the first member 110, the first spring 120, the first cantilever spring 140, and the base member 160.

The first member 110 has a surface that is adapted to engage with an athletic ball (in this example, the basketball 10). In some embodiments, the surface of the first member 110 is contoured with a concavity that matches the outer spherical surface curvature of the basketball 10. The surface of the first member 110 can be textured in some embodiments. Depending on the particular type of object to be engaged with the first member 110, the surface can be adapted in various ways in order to correspond to the shape and size of the particular object.

The first spring 120 is coupled to the first member 110. The first spring 120 is also coupled to the base member 160. Accordingly, as described further below, when the first member 110 pivots in relation to the base member 160 (such as during shooting the basketball 10 using the prosthetic 100) the first spring 120 will deform or deflect. Initially during the shooting motion, the first spring 120 will become compressed. Then later during the shooting motion, the first spring 120 will provide energy return. In other words, the potential or stored energy of the compressed first spring 120 will be released as the first spring 120 extends.

In some embodiments, as described further below, the first spring 120 is constructed to have an electrical conductivity that changes in response to the deflection of the first spring 120. While in the depicted embodiment the first spring 120 is a coil spring, in some embodiments the first spring 120 can be another type of spring such as, but not limited to, a platform leaf spring, a multi-segment platform leaf spring, a bow spring, a cantilever spring, a torsion spring, a variable rate spring, a constant force spring, a constant rate spring, and the like, without limitation.

In the depicted embodiment, the first cantilever spring 140 and the second cantilever spring 150 are not constructed to have an electrical conductivity that changes in response to their deflection or force applied to them. However, in some embodiments one or both of the first cantilever spring 140 and/or the second cantilever spring 150 can be constructed to have an electrical conductivity that changes in response to the deflection(s) thereof. In some such embodiments, the first spring 120 also has such a capability (i.e., to have an electrical conductivity that changes in response to the deflection). Alternatively, in some such embodiments the first spring 120 does not include such a capability.

In some embodiments (such as the depicted embodiment), the prosthetic 100 also includes the second spring 130. The second spring 130 is coupled to the first member 110 and to the base member 160 (like the first spring 120). During the basketball shooting motion using the prosthetic 100, the second spring 130 becomes compressed and then rebounds to provide energy return in the same manner as the first spring 120.

The prosthetic 100 also includes the first cantilever spring 140. The first cantilever spring 140 is attached to and extends from the first member 110. The cantilever spring 140 is deflectable in relation to the first member 110. As described further below, the cantilever spring 140 deflects in relation to the first member 110 and provides energy return during the motion of shooting the basketball 10 using the prosthetic 100. The first cantilever spring 140 has a surface that is arranged to engage with the basketball 10 while the basketball 10 is also engaged with the first member 110. In some embodiments, the surface of the first cantilever spring 140 is contoured with a concavity that matches the outer spherical surface curvature of the basketball 10.

In some embodiments (such as the depicted embodiment), the prosthetic 100 also includes the second cantilever spring 150. The second cantilever spring 150 can be attached to and extend from the first member 110 like the first cantilever spring 140. Also like the first cantilever spring 140, the second cantilever spring 150 is deflectable in relation to the first member 110, and it deflects in relation to the first member 110 and provides energy return during the motion of shooting the basketball 10 using the prosthetic 100. The second cantilever spring 150 also has a surface that is arranged to engage with the basketball 10 while the basketball 10 is also engaged with the first member 110. In some embodiments, the surface of the second cantilever spring 150 is contoured with a concavity that matches the outer spherical surface curvature of the basketball 10.

The prosthetic 100 also includes the base member 160. The first spring 120 and the second spring 130 are coupled to the base member 160. As described further below, the first member 110 is pivotably coupled to the base member 160. The base member 160 also provides a connection point to releasably connect the socket 170 to the base member 160.

The socket 170 defines an interior space configured to receive a residual limb of the user 1. For example, if the arm of the user 1 is amputated below the elbow, the interior space of the socket 170 can be configured to receive a portion of the forearm of the user 1. The socket 170 can be any type of sleeve used by amputees. In some embodiments, the socket 170 includes a connection member configured to releasably connect the socket 170 to the base member 160. For example, in some embodiments the socket 170 includes a threaded rod that can be used to attach the base member 160 to the end of the socket 170.

In some embodiments (such as the depicted embodiment), the prosthetic 100 also includes the electrical circuitry 180. The electrical circuitry 180 can be in one or more housings coupled to the socket 170 and/or the base member 160, in some embodiments.

The electrical circuitry 180 can comprise solid state circuitry (e.g., integrated circuits, transistors, diodes, etc.) and/or analog electrical circuitry. In some embodiments, the electrical circuitry 180 can comprise one or more processors. In some embodiments, the electrical circuitry 180 is programmable. The electrical circuitry 180 can include a power source such as a battery. The electrical circuitry 180 can be configured to receive one or more inputs (such as from electrical connections to measure the conductivity of the first spring 120). The inputs can be digital and/or analog. The electrical circuitry 180 can be configured to provide one or more outputs (such as to the haptic device 190). The outputs can be digital and/or analog. In some embodiments, the outputs can be responsive to the inputs. For example, in the depicted embodiment the output to the haptic device 190 provided by the electrical circuitry 180 can be responsive to the input to the electrical circuitry 180 from the conductivity measurements of the first spring 120. In particular embodiments, an analog output to the haptic device 190 provided by the electrical circuitry 180 can be proportional to an analog input to the electrical circuitry 180 from the conductivity measurements of the first spring 120.

In some embodiments, the circuitry 180 can include a wireless connection such as WiFi, BT, BLE or ANT+ radio that communicates from the arm prosthetic 100 to a smartphone, smartwatch, tablet computer, or another device running an application to provide to the user 1 real-time feedback or post-activity analysis and improvement suggestions. In some embodiments, the application can also include a training tool for the user 1 to visualize how much strain is being applied to each spring of the prosthetic 100 during a shot.

In some embodiments (such as the depicted embodiment), the prosthetic 100 also includes the haptic device 190. In some embodiments, the haptic device 190 can be coupled to the socket 170. In particular embodiments, the haptic device 190 can be coupled to a sock or liner that is worn on a residual limb of the user 1. In still other embodiments, the haptic device 190 can be coupled to other areas of the user 1 or items worn by the user 1.

The haptic device 190 can be various types of devices such as, but not limited to, a vibratory motor, a device that outputs a variable amount of force, an electrotactile device, and the like, without limitation. In some embodiments, the haptic device 190 can be a vibratory motor coupled to the socket 170 and arranged to vibrate against a residual limb of the user 1 within the interior space of the socket 170.

While not required in all embodiments, in some embodiments the prosthetic 100 is made by 3D printing. For example, in some embodiments at least the first member 110, the first spring 120, the second spring 130, the first cantilever spring 140, the second cantilever spring 150, and the base member 160 are all made by 3D printing. In some embodiments, at least the first spring 120 is made by a multi-material 3D printing process, as described further below. In particular embodiments, the prosthetic 100 is made by a single 3D printing process.

In some embodiments, the components of the prosthetic 100 are made by one or more various types of processes (e.g., machining, molding, forming, 3D printing, etc.), and the components are then assembled to form the prosthetic 100.

Figure 6:
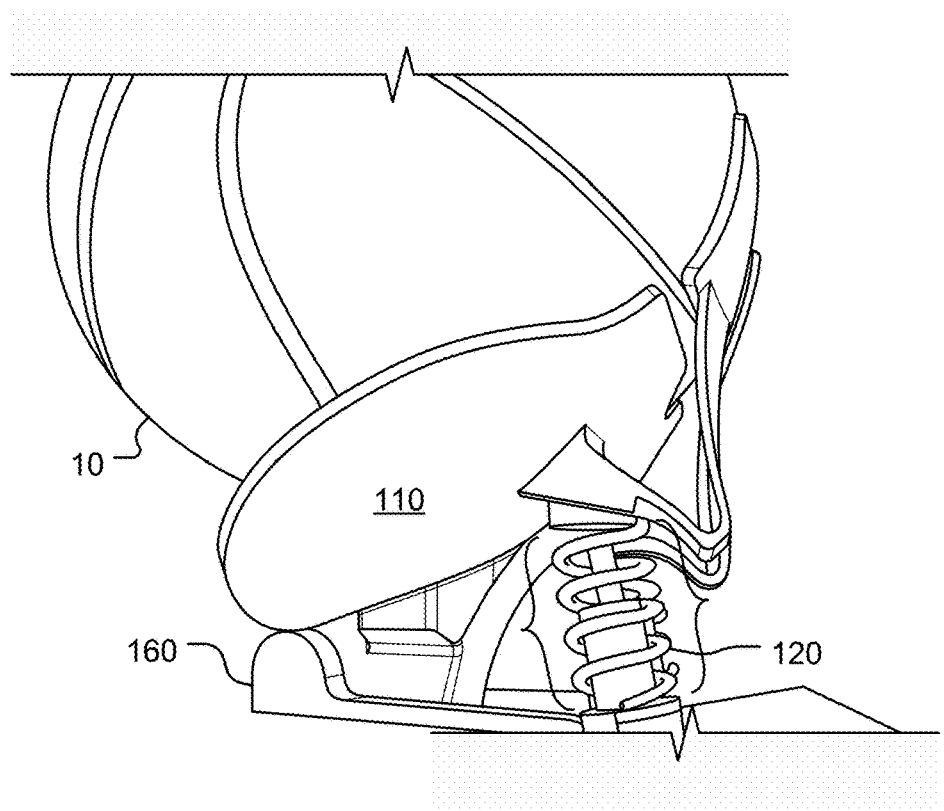
FIG. 6 illustrates the prosthetic hand of FIG. 1 in engagement with the basketball and configured in a first stage of shooting configuration.
Figure 7:
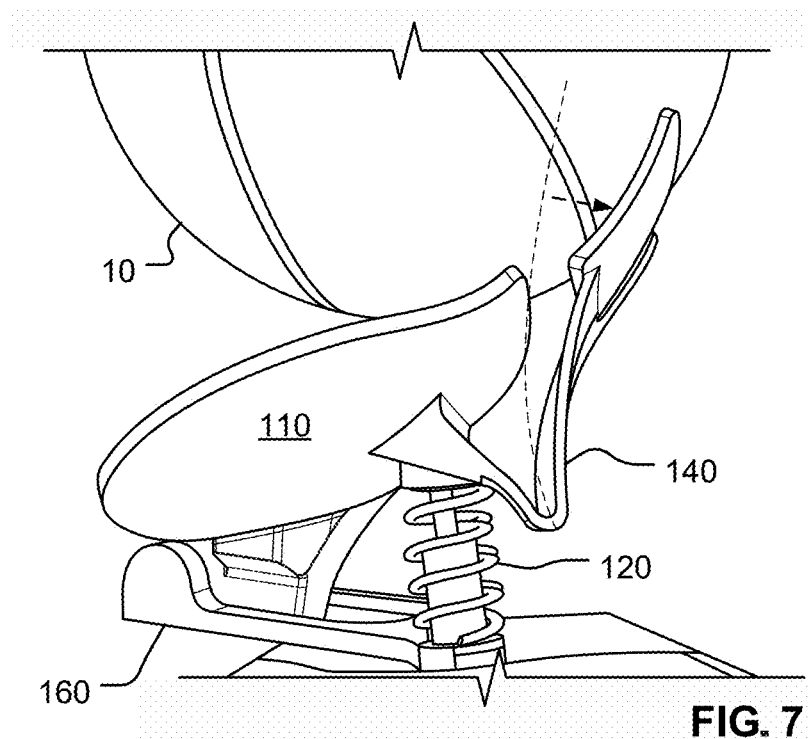
FIG. 7 illustrates the prosthetic hand of FIG. 1 in engagement with the basketball and configured in a second stage of shooting configuration.
Figure 8:
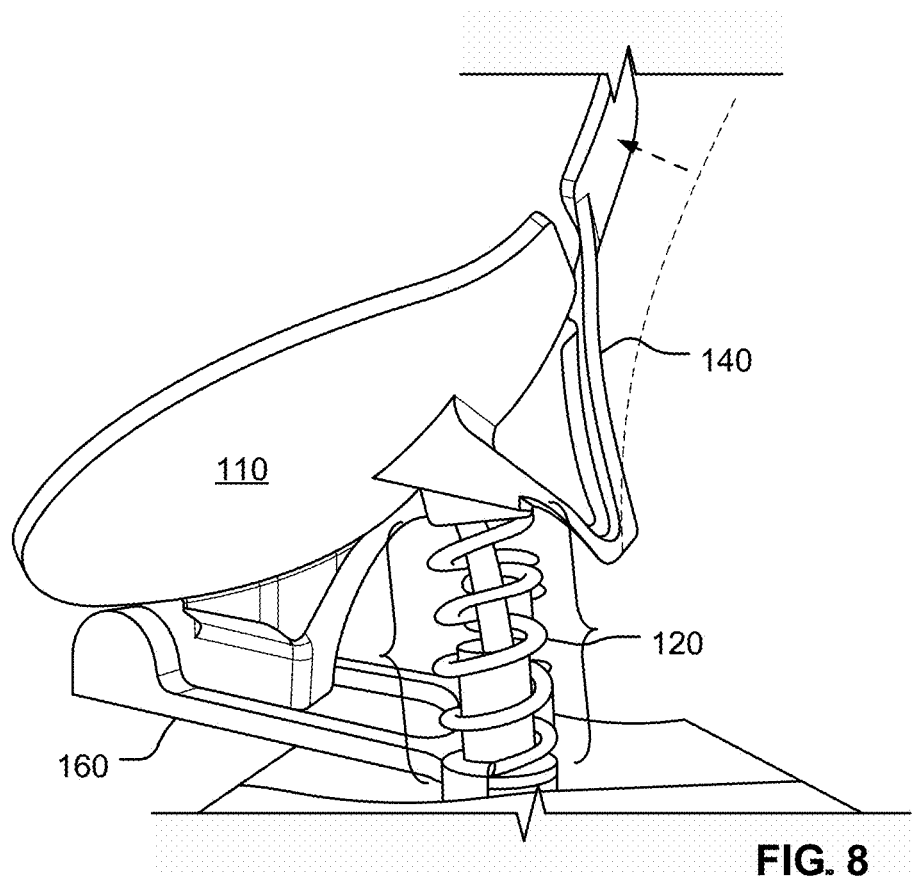
FIG. 8 illustrates the return of the prosthetic hand of FIG. 1 to its natural configuration after the release of the basketball.

FIGS. 6-8 are a series of illustrations depicting the deflections of the springs of the prosthetic 100 during the process of shooting the basketball 10 using the prosthetic 100. The cantilever springs 140/150 and the coil springs 120/130 act as the energy return components. The coil springs 120/130 represents the force generated from wrist flexion, and the cantilever springs 140/150 represents the force generated from finger flexion. Because the index and middle fingers are the last two points to make contact with the basketball 10 in a traditional basketball shot, the prosthetic 100 has two cantilever springs 140/150, corresponding to two fingers. The cantilever springs 140/150 may be curved to match the contour of the first member 110 and the contour of the basketball 10.

A staged deformation between the coil springs 120/130 and the cantilever springs 140/150 may be achieved so the energy return system can closely replicate the biomechanics of a traditional basketball shot. The main upwards force applied by the user 1 goes directly through the center of the coil springs 120/130, and the cantilever springs 140/150 are offset from the main load path. The coil springs 120/130 may be additionally printed with a curved track (as described further below in reference to FIGS. 12 and 13) instead of a linear prismatic joint to match the angle of rotation about the integrated hinge between the first member 110 and the base member 160 (as described further below in reference to FIGS. 9-11).

As depicted in FIG. 6, the basketball shooting motion using the prosthetic 100 causes compression of the first spring 120 (and compression of the second spring 130 if the prosthetic 100 includes the second spring 130). The compression of the first spring 120 is caused by the pivoting of the first member 110 in relation to the base member 160. The pivoting of the first member 110 in relation to the base member 160 is caused by the weight of the basketball 10 (and the first member 110) as the prosthetic 100 is being accelerated upward during the basketball shooting motion using the prosthetic 100.

As described further below, the extent of the compression of the first spring 120 can be detected by monitoring the electrical conductivity of the first spring 120. For example, the electrical circuitry 180 (FIGS. 3 and 4) can be configured and operable to measure/monitor the electrical conductivity of the first spring 120 as the first spring 120 is being compressed during the basketball shooting motion using the prosthetic 100. In some embodiments, the electrical circuitry 180 can provide an output to the haptic device 190 that corresponds (e.g., a proportional output) to the measured/monitored electrical conductivity of the first spring 120. Accordingly, the user of the prosthetic 100 can receive a physical sensation that is indicative of the mount of force being exerted on the basketball 10 during the basketball shooting motion using the prosthetic 100.

As depicted in FIG. 7, the basketball shooting motion using the prosthetic 100 also causes deflection of the first cantilever spring 140 (and deflection of the second cantilever spring 150 if the prosthetic 100 includes the second cantilever spring 150). The deflection of the first cantilever spring 140 is caused by the weight of the basketball 10 as the prosthetic 100 is being accelerated forward during the basketball shooting motion using the prosthetic 100.

As depicted in FIG. 8, the basketball shooting motion using the prosthetic 100 also includes the release of energy (energy return) from the rebound of the first spring 120 (and from the second spring 130, if included) and from the rebound of the first cantilever spring 140 (and from the second cantilever spring 150, if included). The release of the energy provides a basketball shot from the prosthetic 100 that closely simulates a normal basketball shot resulting from the motions of the hands, wrists, and arms of normal shot by a person having all of his/her body parts. For example, the energy return from the first cantilever spring 140 (and from the second cantilever spring 150, if included) provides the last force to the basketball 10, and generates a backspin of the basketball 10 like a natural shot.

As can be now more readily understood in the context of the sequence of FIGS. 6-8, it can be said that the prosthetic 100 includes springs that are arranged in series. That is, the first spring 120 and the first cantilever spring 140 are arranged in series, with the first member 110 arranged between the first spring 120 and the first cantilever spring 140.

FIGS. 9-11 depict an example type of pivotable mechanical connection that can be used between the first member 110 and the base member 160. In the depicted embodiment, the first member 110 includes two opposing conical protrusions 112. The base member defines two opposing conical recesses 162. The conical protrusions 112 movably reside within the conical recesses 162. The interface between the conical protrusions 112 and the conical recesses 162 provide a revolute joint by which the first member 110 is pivotably coupled to the base member 160.

Other arrangements can be used for the pivotable mechanical connection between the first member 110 and the base member 160. For example, in some embodiments the conical protrusions 112 can extend from the base member 160 and the conical recesses 162 can be defined by the first member 110. The conical shape is not required in all embodiments. For example, in some embodiments a cylindrical shape or semi-spherical can be used for the protrusions and recesses.

The pivotable mechanical connection between the first member 110 and the base member 160 can be created during the 3D printing of the first member 110 and the base member 160, if a 3D printing process is used to make the first member 110 and the base member 160. For example, in some embodiments the conical protrusions 112 can be 3D printed within the conical recesses 162 that are defined by 3D printing. In other words, in some embodiments the pivotable mechanical connection between the first member 110 and the base member 160 can be created during a single process/run of 3D printing that creates the first member 110 and the base member 160.

FIGS. 12-15 illustrate additional features of the first spring 120 (which can also be representative of the second spring 130, if included). The depicted first spring 120 includes a coil made of a first material 122 and a second material 124 that are integrated with each other. The first spring 120 also includes a shaft 121 and a guide sleeve 123. The shaft 121 is attached to one end of the first spring 120 and the guide sleeve 123 is attached to the opposite end of the first spring 120.

The shaft 121 movably slides within an internal space defined by the guide sleeve 123. In some embodiments, including the shaft 121 and the guide sleeve 123 can advantageously prevent the first spring 120 from buckling when compressed. These components, while beneficial in some embodiments, are optional. In some embodiments, a dampener is included as part of the assembly of the shaft 121 and the guide sleeve 123. In particular embodiments, the dampener is adjustable so that the user 1 can adjust the amount of dampening.

In the depicted embodiment, the shaft 121 has a polygonal cross-sectional shape and the cross-sectional shape of the internal space defined by the guide sleeve 123 has a corresponding shape (to create a sliding fit therebetween). The polygonal cross-sectional shapes prevent rotations of the shaft 121 relative to the guide sleeve 123. In the depicted embodiment, the polygonal cross-sectional shape is rectangular. However, other polygonal cross-sectional shapes and non-polygonal cross-sectional shapes (e.g., circular) can also be used in some embodiments of the first spring 120.

In some embodiments (e.g., as depicted in FIGS. 12 and 13), the shaft 121 can be curved, and the internal space defined by the guide sleeve 123 can have a corresponding curve. Alternatively, in some embodiments the shaft 121 and the internal space defined by the guide sleeve 123 can be linear (e.g., as depicted in FIGS. 14 and 15).

Figure 14:
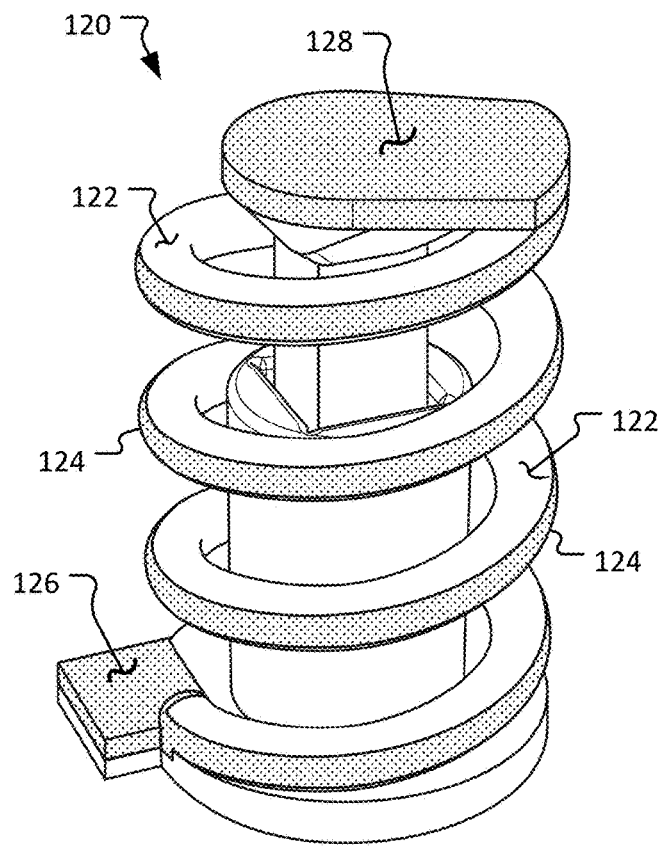
Figure 15:
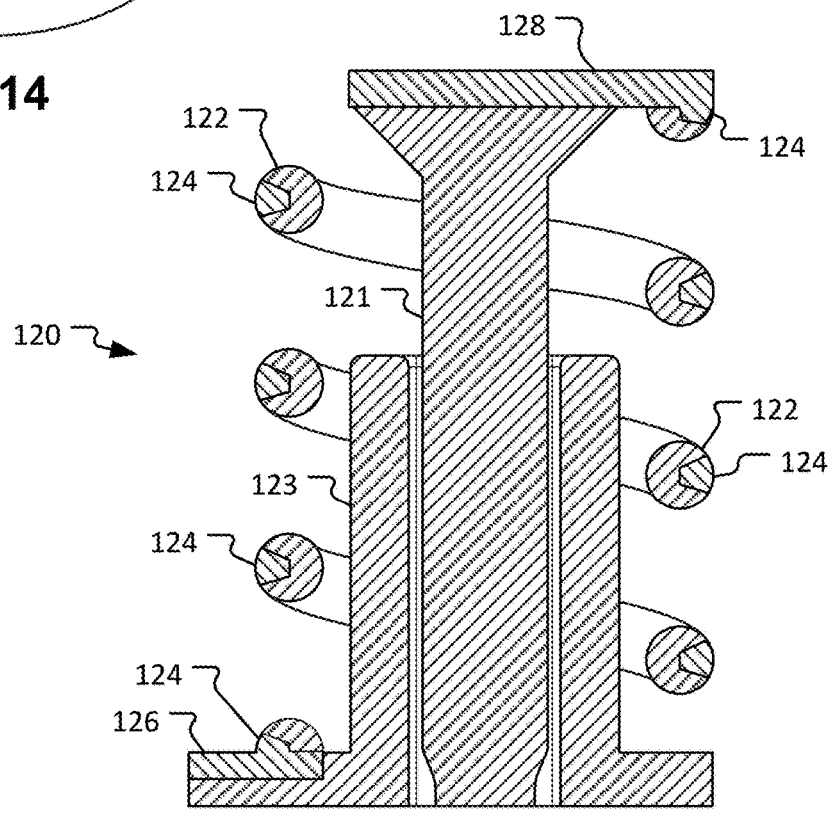

Referring in particular to FIGS. 14 and 15, in some embodiments the first spring 120 can be configured to have an electrical conductivity that changes in response to deformations of the first spring 120. In other words, the first spring 120 can provide an integrated strain sensing capability in addition to providing energy return.

In the depicted embodiment, the first spring 120 is made of at least two different materials. For example, the coil of the first spring 120 includes the first material 122 and the second material 124. The first material 122 and the second material 124 have differing electrical properties. For example, in some embodiments the second material 124 has an electrical conductivity that is greater than an electrical conductivity of the first material 122. In some embodiments, the first material 122 is an electrical insulator and the second material 124 is an electrical conductor.

The first spring 120 is a coil spring and a compression spring. It should be understood, however, that the strain sensing concepts described herein in the context of the first spring 120 (which is a coil compression spring) can also be implemented in many other types of springs. For example, the concepts described herein can be implemented in other types of springs such as, but not limited to, extension springs, torsion springs, cantilevered springs, leaf springs, variable rate springs, constant force springs, constant rate springs, and the like, without limitation.

The first spring 120 can be configured to have any desired spring property including, but not limited to, spring rate, numbers of coils, coil member diameter, pitch, inner and outer diameter of the spring coils, free length, solid length, end types, and the like. Moreover, the first spring 120 can be tuned to generate different desired spring rates and/or force profiles by changing the properties of the first spring 120 as defined by Hooke's Law and Castigliano's theorem. For example, by changing the cross-sectional thickness, the spring diameter, and/or the number of turns (which affect the spring's Young's modulus and shear modulus of a coil spring), the properties of the first spring 120 can be changed. Accordingly, the first spring 120 has the potential to be tuned for a specific end use including, but not limited to, the prosthetic 100.

The first spring 120 also includes a first electrical contact 126 and a second electrical contact 128. The first electrical contact 126 and the second electrical contact 128 are each in electrical communication with the second material 124. At least a portion of the second material 124 extends between the first electrical contact 126 and the second electrical contact 128. In some embodiments, an entirety of the second material 124 extends between the first electrical contact 126 and the second electrical contact 128. In particular embodiments (such as the depicted embodiment), the first electrical contact 126 and the second electrical contact 128 are made of the same type of material as the second material 124. In such a case, the second material 124 and the contacts 122 and 124 are made as a continuous unitary member. In some embodiments, the first electrical contact 126 and/or the second electrical contact 128 are made of a different type of material than the second material 124.

In some embodiments, the first spring 120 is, or comprises, a 3D printed spring or a multi-material 3D printed spring. For example, the first material 122 can be a first 3D printed material, and the second material 124 can be a second 3D printed material that is integrated with the first 3D printed material. In some cases, during at least some portions of the multi-material 3D printing process to make the first spring 120, the first material 122 and the second material 124 are deposited concurrently or simultaneously.

3D printing is a manufacturing technique with emerging areas of research in multi-material 3D printing, metamaterials, and 3D printed electronics. Such techniques can be used to form the first spring 120. The high customizability of a multi-material 3D printing process can make such a process well suited to making the first spring 120 and other components of the prosthetic 100.

A multi-material 3D printed object (e.g., such as the first spring 120 with its first material 122 and second material 124) may refer to an object printed with multiple materials by a multi-material 3D printer. Multi-material 3D printers are capable of consistently printing with multiple materials in the same print. When printing, the material properties of a part are at least somewhat dictated by the material properties of the materials it is printed with.

Metamaterials expands on this capability by allowing parts printed with only one material to have different material properties in multiple sections of the part. This is possible by changing the geometry and internal structure of the print. Metamaterials can enable printing compliant mechanisms and deformable structures without the need for multiple parts. A key application of 3D printed deformable objects is tunable 3D printed helical springs, such as the first spring 120. 3D printing springs introduces the possibility of printing not only deformable objects, but objects with energy return properties.

In some implementations, such as the first spring 120, a conductive material (e.g., from a carbon-based filament) is printed at the same print as traditional material(s) (e.g., from non-conductive filaments). For example, in some embodiments the first spring 120 can be formed by using a multi-material 3D printing process where the first material 122 is made from one or more non-conductive materials and the second material 124 is made from one or more conductive materials (e.g., from one or more carbon-based conductive PLA filaments, silver filaments, graphene filaments, etc.).

As described further below, the first spring 120 is capable of integrated strain sensing, and can be used in combination with the electrical circuitry 180 (FIGS. 3 and 4). The strain-related data from the first spring 120 can be used as either a digital signal or an analog signal.

The first spring 120 is made for absorbing compression and for providing energy return as the first spring 120 rebounds from being compressed as described above. When the first spring 120 is compressed, its coils elastically deform. The deformations of the coils naturally result in stresses and strains in the materials of the coils of the first spring 120 (i.e., the first material 122 and the second material 124). In the depicted embodiment of the first spring 120, both the first material 122 and the second material 124 deform when the first spring 120 is compressed.

The electrical resistance of a conductive material (e.g., the second material 124 in this example) varies with changes in strain of the material. Accordingly, the electrical circuitry 180 can be used to determine or estimate the extent of the deformation of the first spring 120 by monitoring the electrical resistance (or conductivity) of the second material 124, which is strained as the first spring 120 is compressed and/or rebounds from being compressed. In some embodiments, the changes of the electrical resistance/conductivity of the second material 124 in response to the deformation of the first spring 120 are proportional to the extent of deformation of the first spring 120.

The first electrical contact 126 and the second electrical contact 128 are in electrical communication with the second material 124. While the first electrical contact 126 and the second electrical contact 128 are at the ends of the second material 124 in the depicted embodiment, in some embodiments first electrical contact 126 and/or the second electrical contact 128 is/are at locations along the second material 124. At least a portion of the second material 124 (in the coils of the first spring 120) extends between the first electrical contact 126 and the second electrical contact 128. In some embodiments, the first electrical contact 126, the second material 124, and the second electrical contact 128 are all 3D printed from the same material.

The second material 124 inherently has a certain conductivity or resistivity. That conductivity or resistivity varies as the second material 124 is strained or deformed. Accordingly, it follows that the first spring 120 is configured to have an electrical conductivity/resistivity between the first electrical contact 126 and the second electrical contact 128 that changes in response to deformation of the first spring 120. It also follows that by measuring or monitoring the electrical conductivity between the first electrical contact 126 and the second electrical contact 128 using the electrical circuitry 180, the extent of the deformation of the first spring 120 can be determined or estimated.

The materials that make up the 3D printed first spring 120 can be configured in many different ways. In some embodiments, the cross-sectional configuration of the material(s) of the first spring 120 is consistent all along the coils of the first spring 120. In particular embodiments, the cross-sectional configuration of the material(s) of the first spring 120 varies along the coils of the first spring 120 (e.g., the material(s) can be arranged in two of more differing configurations at separate locations along the coils of the first spring 120). Multiple sensor architectures can be used for different applications. Printing with a triangle infill over lines may yield a stiffer spring, and both mechanical and electrical properties may be optimized further to achieve the most elastic response from the coil first spring 120 and the largest and most predictable reading from the integrated strain gauge. This may be made possible by printing the core of a spring with a conductive material that has one infill pattern and density, then a traditional PLA or other material as a shell with a different infill pattern and density for advantageous mechanical properties.

In some embodiments, the coil of the first spring 120 is 3D printed exclusively using the second material 124 (the conductive material) and 100% infill. That is, in some embodiments only the second 3D printed material 124 is between the first electrical contact 126 and the second electrical contact 128. This configuration works well for the highest conductivity to transmit a signal, but may experience little or no change in resistance under loading/strain/deformation. Resistance may increase if the infill percentage is lowered, due to a smaller cross sectional area of conductive material. These implementations may provide more of a digital than an analog output. Because the carbon-based PLA (the second material 124) has such high conductivity, the first spring 120 may not produce a change in resistance throughout the full range of compression. Instead, a change in resistance may only be detected when the first spring 120 is fully compressed.

In some embodiments, to protect the conductive trace of the second 3D printed material 124 from external elements, the conductive trace is printed inside the walls of the first material 122 (e.g., inside the walls of the traditional PLA filament). In other words, the second 3D printed material 124 is encapsulated within the first 3D printed material 100 at one or more locations (or entirely) between the first electrical contact 126 and the second electrical contact 128. By changing the infill density and pattern of the conductive PLA filament (the second 3D printed material 124), the stiffness or spring constant of the first spring 120 can be adjusted.

In some embodiments, the printing of the conductive material (the second 3D printed material 124) comprises an outer portion/segment of the coil, and the rest of the coil is printed with the first 3D printed material 110 (e.g., traditional PLA). In other words, the second 3D printed material 124 between the first electrical contact 126 and the second electrical contact 128 comprises a portion of an outer surface of the first spring 120. In the depicted embodiment (see FIG. 15), the second material 124 comprises about 20% of the outer surface of the coil, and the first material 122 comprises the other 80%. In some embodiments, the second material 124 comprises a majority of the outer surface of the coil. In some embodiments, the first material 122 comprises a majority of the outer surface of the coil. This configuration may be desirable for transmitting a signal through the second material 124 of the coil first spring 120 (e.g., to act as a strain gauge) while retaining the mechanical material properties of the first material 122 (the other non-conductive material) for desired spring characteristics.

In some embodiments, to generate a more analog response (e.g., where the change in resistivity/conductivity of the second material 124 is more directly proportional to the deformation of the first spring 120), conductive PLA filament may be embedded not only in the coil spring, but in other locations such as in the prismatic joint between the first member 110 and the base member 160. By placing the strain sensor in the revolute or prismatic joint, the mechanical material properties of the coil first spring 120 may be tuned to exactly what the application calls for while reading cleaner signals from the sensor. Inspiration may be taken from metamaterials, but by designing open linkages.

Figure 16:
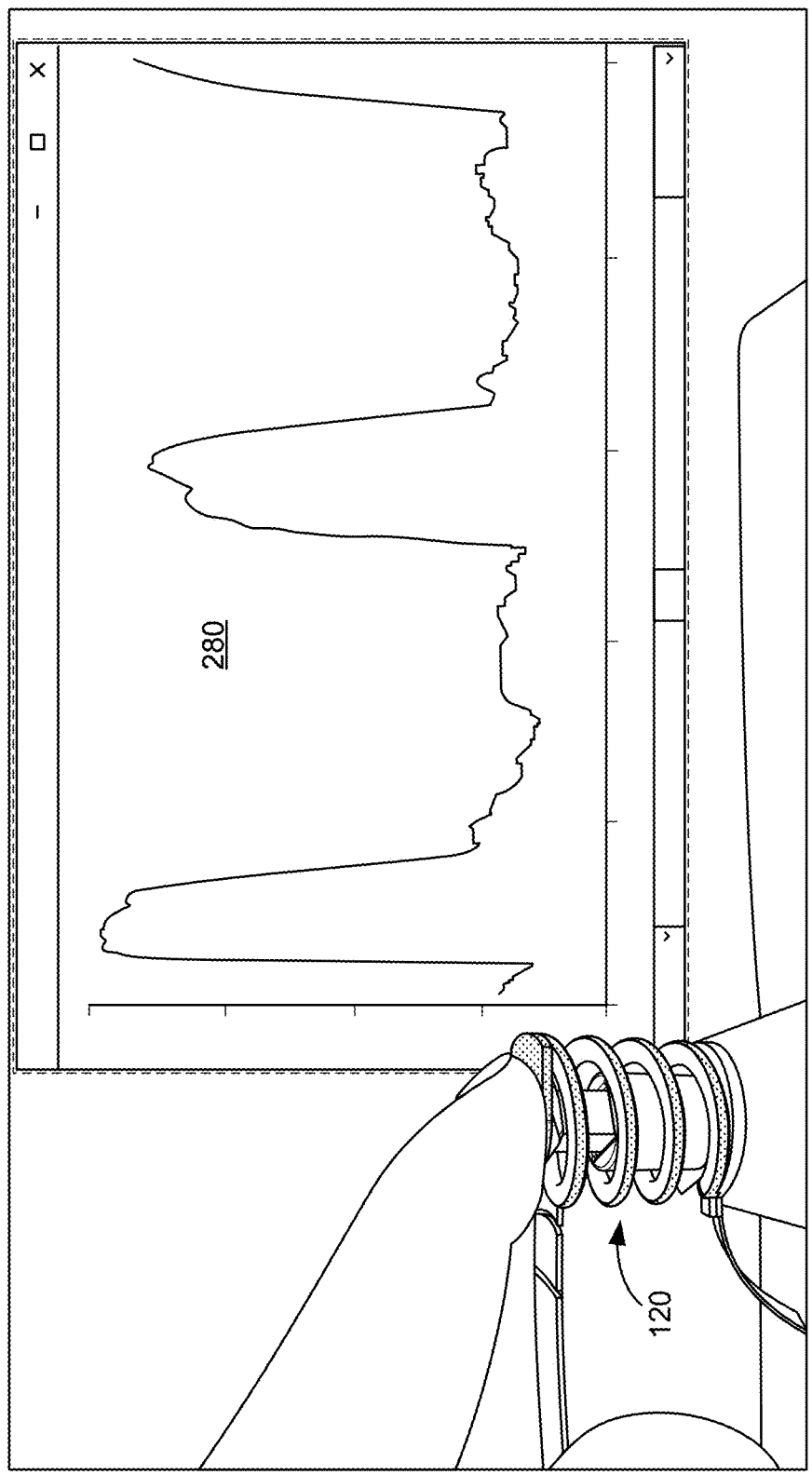
FIG. 16 illustrates the strain sensing functionality of the spring mechanism of FIGS. 12-16.

FIG. 16 illustrates that deformations of the first spring 120 that cause a change in the conductivity/resistivity of the second material 124 can be used to provide an electrical signal for various useful purposes including, but not limited to, providing feedback via the haptic device 190 of the prosthetic 100.

In this example, variances of the electrical signal (in response to variances in the deformation of the first spring 120) are shown in a plot 280. The x-axis of the plot 280 is time and the y-axis is a signal output from the first spring 120 that is responsive to, and indicative of, the deformations of the first spring 120. FIG. 16 shows the change in resistance of the coil first spring 120 during a cycle of relaxation, compression, and relaxation.

In some embodiments, the electrical circuitry 180 can include a Wheatstone bridge used in conjunction with the first spring 120 to provide a variable voltage output from the first spring 120 that is responsive or proportional to the strain of the second material 124 (and responsive or proportional to the deformation of the first spring 120).

Strain may be measured through a change in resistance of the conductive coil (the second material 124) of the first spring 120. In some embodiments, the resistance may be read through the analog input of an Adafruit Metro Mini 328 microcontroller and smoothed using a moving average filter with a window size of 10, for example.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results.

What is claimed is:

1. An upper-extremity prosthetic comprising:
a first member having a surface adapted to engage with an athletic ball;
a first spring coupled to the first member, the first spring arranged to absorb energy and to provide energy return in response to movement of the first member, wherein the first spring comprises a coil spring including a first portion made of a first material and a second portion made of a second material that is electrically conductive, wherein the second portion comprises a portion of an outer surface of the first spring and is at least partially encapsulated within the first material along a length of the coil spring, and wherein the second portion has an electrical conductivity that: (i) is greater than an electrical conductivity of the first portion and (ii) changes in response to deflection of the first spring; and
electrical circuitry configured to measure the electrical conductivity of the second portion and to output a signal responsive to the measured electrical conductivity.

2. The prosthetic of claim 1, further comprising a base member coupled to the first spring and pivotably coupled to the first member, wherein pivoting the first member relative to the base member deflects the first spring.

3. The prosthetic of claim 2, further comprising:
a sleeve coupled to the base member and defining an interior space configured to receive a residual limb of a user of the prosthetic; and
a haptic device arranged to receive the signal responsive to the electrical conductivity from the electrical circuitry, wherein the haptic device is a vibratory motor arranged to vibrate against a residual limb in the interior space.

4. The prosthetic of claim 1, further comprising a first cantilever spring coupled to the first member and including a surface arranged to engage with an athletic ball engaged with the first member.

5. The prosthetic of claim 1, further comprising a first cantilever spring coupled to the first member and a second cantilever spring coupled to the first member, wherein the first and second cantilever springs each include a surface arranged to engage with an athletic ball engaged with the first member.

6. The prosthetic of claim 5, wherein the surfaces of the first member, the first cantilever spring, and the second cantilever spring are each contoured to engage with an athletic ball.

7. The prosthetic of claim 1, wherein the first spring is a multi-material 3D printed device, and wherein the first and second portions are 3D printed in a single print process.

8. The prosthetic of claim 7, wherein the first spring and the first member are 3D printed in the single print process.

9. An upper-extremity prosthetic comprising:
a first member having a surface adapted to engage with an athletic ball;
a first spring coupled to the first member and arranged to deflect and to provide energy return in response to movement of the first member, wherein the first spring comprises a coil spring including a first portion made of a first material and a second portion made of a second material that is electrically conductive, wherein the second portion comprises a portion of an outer surface of the first spring and is at least partially encapsulated within the first material along a length of the coil spring, and wherein the second portion has an electrical conductivity that: (i) is greater than an electrical conductivity of the first portion and (ii) changes in response to deflection of the first spring;
a base member coupled to the first spring and pivotably coupled to the first member at a revolute joint, wherein the revolute joint comprises a pair of conical protrusions that movably reside within a pair of conical recesses;
a guide sleeve defining an internal space;
a shaft slidably extending within the internal space, wherein the first spring winds around the guide sleeve and the shaft, wherein the shaft and the internal space are each curved to match an arc defined by rotation of the revolute joint between the first member and the base member; and a first cantilever spring extending from the first member and having a surface adapted to engage with an athletic ball while the athletic ball is also engaged with the surface of the first member.

10. The prosthetic of claim 9, further comprising a second cantilever spring extending from the first member and having a surface adapted to engage with an athletic ball while the athletic ball is also engaged with the surface of the first member.

11. The prosthetic of claim 9, further comprising a second spring coupled to the first member and arranged to deflect and to provide energy return in response to movement of the first member.

12. The prosthetic of claim 11, wherein the first and second springs are spring is a coil spring.

13. The prosthetic of claim 9, wherein pivoting the first member relative to the base member deflects the first spring.

14. The prosthetic of claim 13, further comprising a sleeve coupled to the base member and defining an interior space configured to receive a residual limb of a user of the prosthetic.

15. The prosthetic of claim 13, wherein the base member, the first member, the first spring, and the first cantilever spring member are each 3D printed in a single print process.

16. The prosthetic of claim 15, wherein the first spring is a multi-material 3D printed device and comprises:

a first electrical contact connected to the second portion 3D printed material; and a second electrical contact connected to the second portion.

17. The prosthetic of claim 16, further comprising electrical circuitry configured to detect the electrical conductivity of the first spring between the first and second electrical contacts and to output a signal responsive to the electrical conductivity.

18. The prosthetic of claim 17, further comprising a haptic device arranged to receive the signal responsive to the electrical conductivity from the electrical circuitry, and wherein the haptic device is a vibratory motor arranged to vibrate against a limb of a user of the prosthetic.

19. The prosthetic of claim 9, wherein the shaft has a polygonal cross-sectional shape and the internal space has a corresponding polygonal cross-sectional shape to prevent rotations of the shaft relative to the guide sleeve.

* * * * *

UNITED STATES PATENT AND TRADEMARK OFFICE
CERTIFICATE OF CORRECTION

| | |
|---|---|
| PATENT NO. | : 11,969,362 B2 |
| APPLICATION NO. | : 17/242632 |
| DATED | : April 30, 2024 |
| INVENTOR(S) | : Mark Benjamin Greenspan and Lavinia Andreea Danielescu |

It is certified that error appears in the above-identified patent and that said Letters Patent is hereby corrected as shown below:

In the Claims

In Claim 12, Column 15, Line 18, after "the" delete "first and".

In Claim 12, Column 15, Line 19, after "second" delete "springs are".

In Claim 16, Column 16, Line 6-7, delete "portion 3D printed material;" and insert -- portion; --.

Signed and Sealed this
Second Day of July, 2024

Katherine Kelly Vidal
*Director of the United States Patent and Trademark Office*